United States Patent
Curley et al.

(10) Patent No.: US 9,877,768 B2
(45) Date of Patent: Jan. 30, 2018

(54) METHODS AND DEVICES FOR HEATING FLUID IN FLUID ENHANCED ABLATION THERAPY

(71) Applicant: Thermedical, Inc., Waltham, MA (US)

(72) Inventors: Michael G. Curley, Weston, MA (US); Fredrick J. Kim, Cambridge, MA (US)

(73) Assignee: Thermedical, Inc., Waltham, MA (US)

( * ) Notice: Subject to any disclaimer, the term of this patent is extended or adjusted under 35 U.S.C. 154(b) by 0 days.

(21) Appl. No.: 14/826,549

(22) Filed: Aug. 14, 2015

(65) Prior Publication Data

US 2015/0359582 A1    Dec. 17, 2015

Related U.S. Application Data

(63) Continuation of application No. 13/445,036, filed on Apr. 12, 2012, now Pat. No. 9,138,287.

(Continued)

(51) Int. Cl.
    *A61B 18/08*    (2006.01)
    *A61B 18/04*    (2006.01)
    (Continued)

(52) U.S. Cl.
    CPC ............ *A61B 18/04* (2013.01); *A61B 18/082* (2013.01); *A61B 18/1477* (2013.01);
    (Continued)

(58) Field of Classification Search
    CPC ................................. A61B 2018/00654; A61B 2018/044–2018/048; A61B 2018/1273;
    (Continued)

(56) References Cited

U.S. PATENT DOCUMENTS

| 4,160,455 A | 7/1979 | Law |
| 4,424,190 A | 1/1984 | Mather, III et al. |

(Continued)

FOREIGN PATENT DOCUMENTS

| CN | 1341462 A | 3/2002 |
| CN | 1119127 C | 8/2003 |

(Continued)

OTHER PUBLICATIONS

Chinese Office Action for Application No. 201280028621.X, issued Jul. 31, 2015. (18 pages).

(Continued)

*Primary Examiner* — Michael Kahelin
(74) *Attorney, Agent, or Firm* — Nutter McClennen & Fish LLP

(57) ABSTRACT

Devices and methods for efficiently and reproducibly heating fluid for use in fluid enhanced ablation are disclosed herein. In one embodiment, an ablation device is provided having an elongate body, at least one wire extending through an inner lumen of the elongate body, and at least one spacer disposed within the inner lumen. The at least one wire extends through the at least one spacer such that the at least one spacer is effective to maintain an adjacent portion of the at least one wire in a substantially fixed geometric relationship with the inner lumen, thereby preventing electrical shorts and providing for the consistent and uniform heating of fluid flowing through the inner lumen of the elongate body.

20 Claims, 12 Drawing Sheets

Related U.S. Application Data

(60) Provisional application No. 61/474,574, filed on Apr. 12, 2011.

(51) Int. Cl.
*A61B 18/14* (2006.01)
*A61B 18/00* (2006.01)
*A61B 17/00* (2006.01)

(52) U.S. Cl.
CPC .............. *A61B 2017/00526* (2013.01); *A61B 2018/00029* (2013.01); *A61B 2018/00577* (2013.01); *A61B 2018/00642* (2013.01); *A61B 2018/00773* (2013.01); *A61B 2018/00791* (2013.01); *A61B 2018/00797* (2013.01); *A61B 2018/00809* (2013.01); *A61B 2018/00821* (2013.01); *A61B 2018/046* (2013.01); *A61B 2018/1425* (2013.01); *F04C 2270/041* (2013.01); *Y10T 29/49016* (2015.01); *Y10T 29/49085* (2015.01)

(58) Field of Classification Search
CPC .......... A61B 5/04001; A61N 1/0529; A61N 1/0558; A61N 1/0531; A61N 1/0534; A61N 1/0536; A61N 1/36082; A61N 1/0539
See application file for complete search history.

(56) References Cited

U.S. PATENT DOCUMENTS

| | | |
|---|---|---|
| 5,190,538 A | 3/1993 | Hussein et al. |
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,437,629 A | 8/1995 | Goldrath |
| 5,437,673 A | 8/1995 | Baust et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,609,151 A | 3/1997 | Mulier et al. |
| 5,653,692 A | 8/1997 | Masterson et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,233,490 B1 | 5/2001 | Kasevich |
| 6,238,393 B1 | 5/2001 | Mulier et al. |
| 6,272,370 B1 | 8/2001 | Gillies et al. |
| 6,302,904 B1 | 10/2001 | Wallsten et al. |
| 6,315,777 B1 | 11/2001 | Comben |
| 6,328,735 B1 | 12/2001 | Curley et al. |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Sharkey et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,559,905 B2 | 7/2009 | Kagosaki et al. |
| 7,604,634 B2 | 10/2009 | Hooven |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 2001/0031946 A1 | 10/2001 | Walker et al. |
| 2002/0120259 A1 | 8/2002 | Lettice et al. |
| 2002/0123749 A1 | 9/2002 | Jain |

(56) References Cited

U.S. PATENT DOCUMENTS

| | | |
|---|---|---|
| 2002/0153046 A1 | 10/2002 | Dantsker et al. |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0058386 A1 | 2/2014 | Clark et al. |
| 2014/0188106 A1 | 7/2014 | Curley |
| 2014/0275977 A1 | 9/2014 | Curley et al. |
| 2014/0276743 A1 | 9/2014 | Curley |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2016/0354138 A1 | 12/2016 | Curley |

FOREIGN PATENT DOCUMENTS

| | | |
|---|---|---|
| CN | 1525839 A | 9/2004 |
| CN | 1897885 A | 1/2007 |
| CN | 101209217 A | 7/2008 |
| CN | 101578073 A | 11/2009 |
| CN | 101773699 A | 7/2010 |
| CN | 201642316 U | 11/2010 |
| CN | 101999931 A | 4/2011 |
| EP | 0 895 756 A1 | 2/1999 |
| EP | 1 033 107 A1 | 9/2000 |
| EP | 0 908 156 B1 | 11/2003 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 02/089686 A1 | 11/2002 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Extended European Search Report and Search Opinion for Application No. 13829821.1 issued Mar. 17, 2016 (7 pages).
Japanese Office Action for Application No. 2014-505266, mailed Feb. 23, 2016 (7 pages).
Brace CL. Microwave tissue ablation: biophysics, technology, and applications.; Crit Rev Biomed Eng. 2010;38 (1):65-78.
Chinese Office Action for Application No. 201280028609.9, issued May 27, 2015 (22 pages).
Chinese Office Action for Application No. 201280028611.6, issued Jul. 29, 2015. (23 pages).
Chinese Office Action for Application No. 201280028620.5, issued May 27, 2015. (26 pages).
Extended Search Report and Written Opinion for EP 12 77 0537 dated Oct. 2, 2014 (6 pages).
Extended Search Report and Written Opinion for EP 12770631.5 dated Oct. 1, 2014 (6 Pages).
Extended Search Report and Written Opinion for EP 12771331.1 dated Sep. 25, 2014 (6 Pages).
Extended European Search Report and Written Opinion for Application No. 12771601.7 issued Oct. 27, 2014 (7 pages).
Extended Search Report and Written Opinion for EP 12 77 1876 dated Oct. 7, 2014 (6 pages).
International Search Report and Written Opinion for Application No. PCT/US2012/033203, issued Sep. 21, 2012. (23 pages).
International Search Report and Written Opinion for Application No. PCT/US2012/033213, issued Sep. 21, 2012. (17 pages).
International Search Report and Written Opinion for Application No. PCT/US2012/033216, issued Sep. 21, 2012. (17 pages).
International Search Report and Written Opinion for Application No. PCT/US2012/033327, issued Sep. 21, 2012. (14 pages).
International Search Report and Written Opinion for Application No. PCT/US2012/033332, issued Sep. 21, 2012. (20 pages).
International Search Report and Written Opinion for Application No. PCT/US2013/053977, issued Nov. 14, 2013. (20 pages).

(56) References Cited

OTHER PUBLICATIONS

International Search Report and Written Opinion for Application No. PCT/US2014/024731, mailed Jul. 21, 2014 (39 pages).
David R. Lide (ed)., CRC Handbook of Chemistry and Physics, 87th Edition. 2006. p. 8-81 CRC Press, Florida.
Nath et al., Prog. Card Dis. 37(4):185-205 (1995).
Rolf Sander, Compilation of Henry's Law Constants for Inorganic and Organic Species of Potential Importance in Environmental Chemistry. Max-Planck Institute of Chemistry 1999, Mainz Germany. Www.henrys-law.org.
Sapareto et al., Int. J Rad. One. Biol. Phys. 10(6):787-800 (1984).
Chinese Office Action for Application No. 201380053690.0, issued Sep. 30, 2016. (17 pages).
U.S. Appl. No. 15/450,806, filed Mar. 6, 2017, Devices and Methods for Remote Temperature Monitoring in Fluid Enhanced Ablation Therapy.
Young, S.T., et al., An instrument using variation of resistance to aid in needle tip insertion in epidural block in monkeys. Med Instrum. Oct. 1987;21(5):266-8. Abstract Only.
U.S. Appl. No. 15/234,858, filed Aug. 11, 2016, Devices and Methods for Delivering Fluid to Tissue During Ablation Therapy.
U.S. Appl. No. 15/240,693, filed Aug. 18, 2016, Methods and Devices for Controlling Ablation Therapy.
Japanese Office Action for Application No. 2014-505263, mailed Jan. 26, 2016 (4 pages).
U.S. Appl. No. 13/445,034, filed Apr. 12, 2012, Devices and Methods for Remote Temperature Monitoring in Fluid Enhanced Ablation Therapy.
U.S. Appl. No. 13/445,036, filed Apr. 12, 2012, Methods and Devices for Heating Fluid in Fluid Enhanced Ablation Therapy.
U.S. Appl. No. 13/445,040, filed Apr. 12, 2012, Methods and Devices for Use of Degassed Fluids With Fluid Enhanced Ablation Devices.
U.S. Appl. No. 13/445,365, filed Apr. 12, 2012, Devices and Methods for Shaping Therapy in Fluid Enhanced Ablation.
U.S. Appl. No. 13/445,373, filed Apr. 12, 2012, Methods and Devices for Controlling Ablation Therapy.
U.S. Appl. No. 13/586,559, filed Aug. 15, 2012, Low Profile Fluid Enhanced Ablation Therapy Devices and Methods.
U.S. Appl. No. 13/837,295, filed Mar. 15, 2013, Methods and Devices for Fluid Enhanced Microwave Ablation Therapy.
U.S. Appl. No. 13/842,561, filed Mar. 15, 2013, Systems and Methods for Visualizing Fluid Enhanced Ablation Therapy.
U.S. Appl. No. 14/202,425, filed Mar. 10, 2014, Devices and Methods for Shaping Therapy in Fluid Enhanced Ablation.
U.S. Appl. No. 14/536,212, filed Nov. 7, 2014, Methods and Devices for Use of Degassed Fluids With Fluid Enhanced Ablation Devices.
U.S. Appl. No. 14/688,790, filed Apr. 16, 2015, Methods and Devices for Fluid Enhanced Microwave Ablation Therapy.
U.S. Appl. No. 14/826,563, filed Aug. 14, 2015, Methods and Devices for Use of Degassed Fluids With Fluid Enhanced Ablation Devices.
Chinese Office Action for Application No. 201280028612.0, dated Nov. 2, 2016. (8 pages).
Chinese Office Action for Application No. 201380053690.0, dated Jul. 20, 2017. (18 pages).

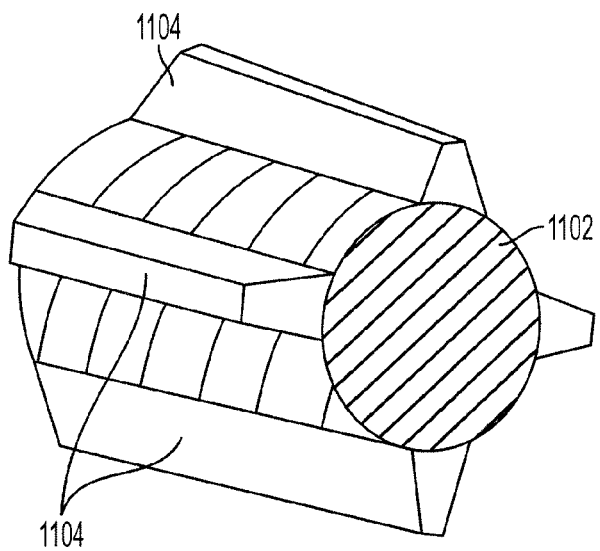
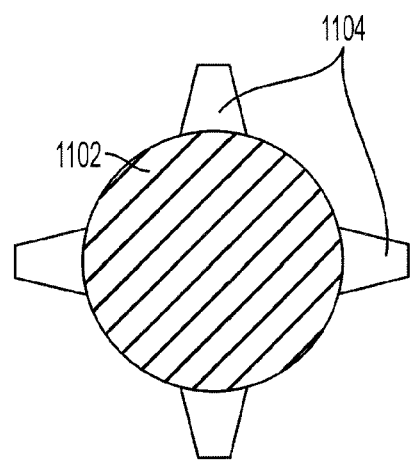
FIG. 11A  FIG. 11B
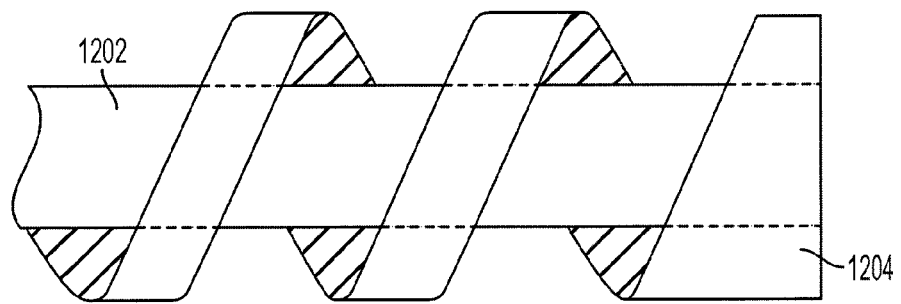
FIG. 12

METHODS AND DEVICES FOR HEATING FLUID IN FLUID ENHANCED ABLATION THERAPY

This application is a continuation of U.S. application Ser. No. 13/445,036, filed Apr. 12, 2012, and entitled "Methods and Devices for Heating Fluid in Fluid Enhanced Ablation Therapy," now issued as U.S. Pat. No. 9,138,287, which claims priority to U.S. Provisional Application Ser. No. 61/474,574, filed on Apr. 12, 2011, and entitled "Improvement in Ablation Catheters." This application is also related to U.S. application Ser. No. 13/445,034 entitled "Devices and Methods for Remote Temperature Monitoring in Fluid Enhanced Ablation Therapy," U.S. application Ser. No. 13/445,365 "Devices and Methods for Shaping Therapy in Fluid Enhanced Ablation," now issued as U.S. Pat. No. 8,702,697, U.S. application Ser. No. 13/445,373 "Methods and Devices for Controlling Ablation Therapy," now issued as U.S. Pat. No. 9,445,861, and U.S. application Ser. No. 13/445,040 "Methods and Devices for Use of Degassed Fluids with Fluid Enhanced Ablation Devices," now issued as U.S. Pat. No. 8,945,121, respectively, and filed concurrently with the present application. The disclosures of each of these applications are hereby incorporated by reference in their entirety.

GOVERNMENT RIGHTS

This invention was made with government support under grants CA69926 and HL63535 awarded by The National Institutes of Health. The government has certain rights in the invention.

FIELD

This invention relates generally to fluid enhanced ablation, such as the SERF™ ablation technique (Saline Enhanced Radio Frequency™ ablation). More particularly, this invention relates to improved devices and methods for heating assemblies used to heat fluid introduced into tissue during ablation.

BACKGROUND

The use of thermal energy to destroy bodily tissue can be applied to a variety of therapeutic procedures, including the destruction of tumors. Thermal energy can be imparted to the tissue using various forms of energy, such as radio frequency electrical energy, microwave or light wave electromagnetic energy, or ultrasonic vibrational energy. Radio frequency (RF) ablation, for example, can be effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, maximum heating can occur in the tissue immediately adjacent to the emitting electrode. This can reduce the conductivity of the tissue, and in some cases, can cause water within the tissue to boil and become water vapor. As this process continues, the impedance of the tissue can increase and prevent current from entering into the surrounding tissue. Thus, conventional RF instruments are limited in the volume of tissue that can be treated.

Fluid enhanced ablation therapy, such as the SERF™ ablation technique (Saline Enhanced Radio Frequency™ ablation), can treat a greater volume of tissue than conventional RF ablation. The SERF ablation technique is described in U.S. Pat. No. 6,328,735, which is hereby incorporated by reference in its entirety. Using the SERF ablation technique, saline is passed through a needle and heated, and the heated fluid is delivered to the tissue immediately surrounding the needle. The saline helps distribute the heat developed adjacent to the needle and thereby allows a greater volume of tissue to be treated with a therapeutic dose of ablative energy. The therapy is usually completed once a target volume of tissue reaches a desired therapeutic temperature, or otherwise receives a therapeutic dose of energy.

During fluid enhanced ablation therapy, the fluid can be heated to a desired temperature in a variety of different ways. For example, the fluid can be heated remotely from the needle and then pumped into the needle at an elevated temperature. However, transferring heated fluid can result in undesirable temperature loss between the remote heater and the treatment site, as well as undesirable heating of remote portions of the patient's body. Alternatively, the fluid can be heated after it enters the needle and prior to injection into the tissue. However, it can be difficult to construct and repeatedly manufacture a heating assembly capable of disposition within the sometimes very small needle bodies used in fluid enhanced ablation. Furthermore, the needle body itself is a conductive material used to deliver energy to the treatment site, so precautions must be taken to avoid interfering with energy passed through the needle body.

Accordingly, there remains a need for improved devices and methods for heating fluid used during fluid enhanced ablation therapy.

SUMMARY

The present invention generally provides devices and methods for reliably and uniformly heating fluid for use in fluid enhanced ablation devices. In one aspect of the invention, an ablation device is provided that includes an elongate body having proximal and distal ends, an inner lumen extending through the elongate body, and at least one outlet port formed in the elongate body that is configured to deliver fluid to tissue surrounding the elongate body. The device also includes at least one wire extending through the inner lumen, the at least one wire being configured to heat fluid flowing through the inner lumen, and at least one spacer disposed within the inner lumen. The at least one spacer is effective to maintain an adjacent portion of the at least one wire in a substantially fixed geometric relationship with the inner lumen.

The ablation device described above can have a variety of modifications that are within the scope of the invention. For example, in some embodiments, the device can also include an ablation element disposed along a length of the elongate body adjacent to the at least one outlet port, and the ablation element can be configured to heat tissue surrounding the ablation element when the elongate body is inserted into tissue. In other embodiments, the at least one wire and the at least one spacer can be positioned proximal of the ablation element.

In certain embodiments, the at least one spacer can include a first spacer and a second spacer. The first spacer can be positioned at a proximal end of a distal portion of the at least one wire, and the second spacer can be positioned at a distal end of the distal portion of the at least one wire. In some embodiments, the first and second spacers can be positioned a distance apart from one another, and the distance can be about 5 mm. In other embodiments, the distance can be about 2 mm. In some other embodiments, a portion of the at least one wire extending between the first and second spacers can be configured to heat fluid flowing through the inner lumen.

In still other embodiments, the at least one spacer can include a disc-shaped member and the at least one wire can include first and second wires configured to extend through first and second bores in the spacer. In some embodiments, the at least one spacer can include at least one protrusion formed on the at least one wire.

In some other embodiments, the at least one spacer can prevent the at least one wire from contacting the inner lumen of the elongate body. In certain embodiments, the at least one wire can be insulated proximal to the at least one spacer to prevent contact with the inner lumen of the elongate body. In still other embodiments, the inner lumen can be lined with an insulating layer to prevent the at least one wire from contacting an inner wall of the elongate body.

In other embodiments, the at least one spacer can have a maximum outer diameter that is less than a diameter of the inner lumen such that the at least one spacer can move radially within the inner lumen. In still other embodiments, the at least one spacer can have a maximum outer diameter equal to a diameter of the inner lumen such that the at least one spacer cannot move radially within the inner lumen. In certain embodiments, the at least one spacer can be configured to maintain the at least one wire in a position substantially coaxial with a longitudinal axis of the elongate body.

In some embodiments, the ablation device can further include at least one temperature sensor disposed within the inner lumen distal to the at least one spacer and configured to measure a temperature of the fluid flowing through the inner lumen. In some other embodiments, the ablation device can further include a second temperature sensor disposed within the inner lumen proximal to the at least one spacer and configured to measure a temperature of the fluid flowing through the inner lumen before being heated. In some embodiments, the temperature sensors can be thermocouples. In still other embodiments, the at least one temperature sensor can be separated from the at least one spacer by a distance of about 10 mm. In other embodiments, the at least one temperature sensor can be separated from the at least one spacer by a distance of about 2 mm.

In another aspect of the invention, a method of ablating tissue is provided that includes inserting an elongate body into a tissue mass and delivering fluid through an inner lumen of the elongate body such that the fluid flows through at least one outlet port in the elongate body and into the tissue mass. The method can further include delivering energy through at least one wire extending through the inner lumen to uniformly heat the fluid within the lumen to a predetermined temperature.

In some embodiments, delivering energy through at least one wire can include passing energy between two or more wires extending through the inner lumen. In other embodiments, delivering energy through at least one wire can include passing energy between one or more wires and the elongate body or between one or more wires and a conductive tube contained within the elongate body. In still other embodiments, the method can further include delivering energy into the tissue mass from at least one ablation element positioned adjacent to the at least one outlet port.

In another aspect of the invention, a method for manufacturing a plurality of ablation devices is provided that includes forming a first ablation device by positioning a first heating assembly within a first elongate body, the first heating assembly having at least one wire extending through at least one spacer. The method can further include forming a second ablation device by positioning a second heating assembly within a second elongate body, the second heating assembly having at least one wire extending through at least one spacer. Further, the electrical resistance of the first heating assembly can be substantially identical to the electrical resistance of the second heating assembly.

In still another aspect of the invention, an ablation device is provided that includes an elongate body having proximal and distal ends, an inner lumen extending through the elongate body, and at least one outlet port formed in the elongate body configured to deliver fluid to tissue surrounding the elongate body. The device also includes a heating assembly that includes at least two wires extending through the inner lumen, the at least two wires being configured to heat fluid flowing through the inner lumen. Further, the device includes at least one spacer disposed within the inner lumen. The at least two wires extend through the at least one spacer such that the at least one spacer is effective to maintain the at least two wires in a substantially fixed geometric relationship with each other. In some embodiments, the device can further include an ablation element disposed along a length of the elongate body adjacent to the at least one outlet port, and the ablation element can be configured to heat tissue surrounding the ablation element when the elongate body is inserted into tissue.

BRIEF DESCRIPTION OF THE DRAWINGS

The aspects and embodiments of the invention described above will be more fully understood from the following detailed description taken in conjunction with the accompanying drawings, in which:

FIG. 11A is a diagram of an alternative embodiment of a spacer element formed on a wire;

FIG. 11B is a cross-sectional diagram of the wire and spacer element of FIG. 11A;

FIG. 12 is a diagram of an alternative embodiment of a spacer element formed on a wire;

DETAILED DESCRIPTION

Figure 1:
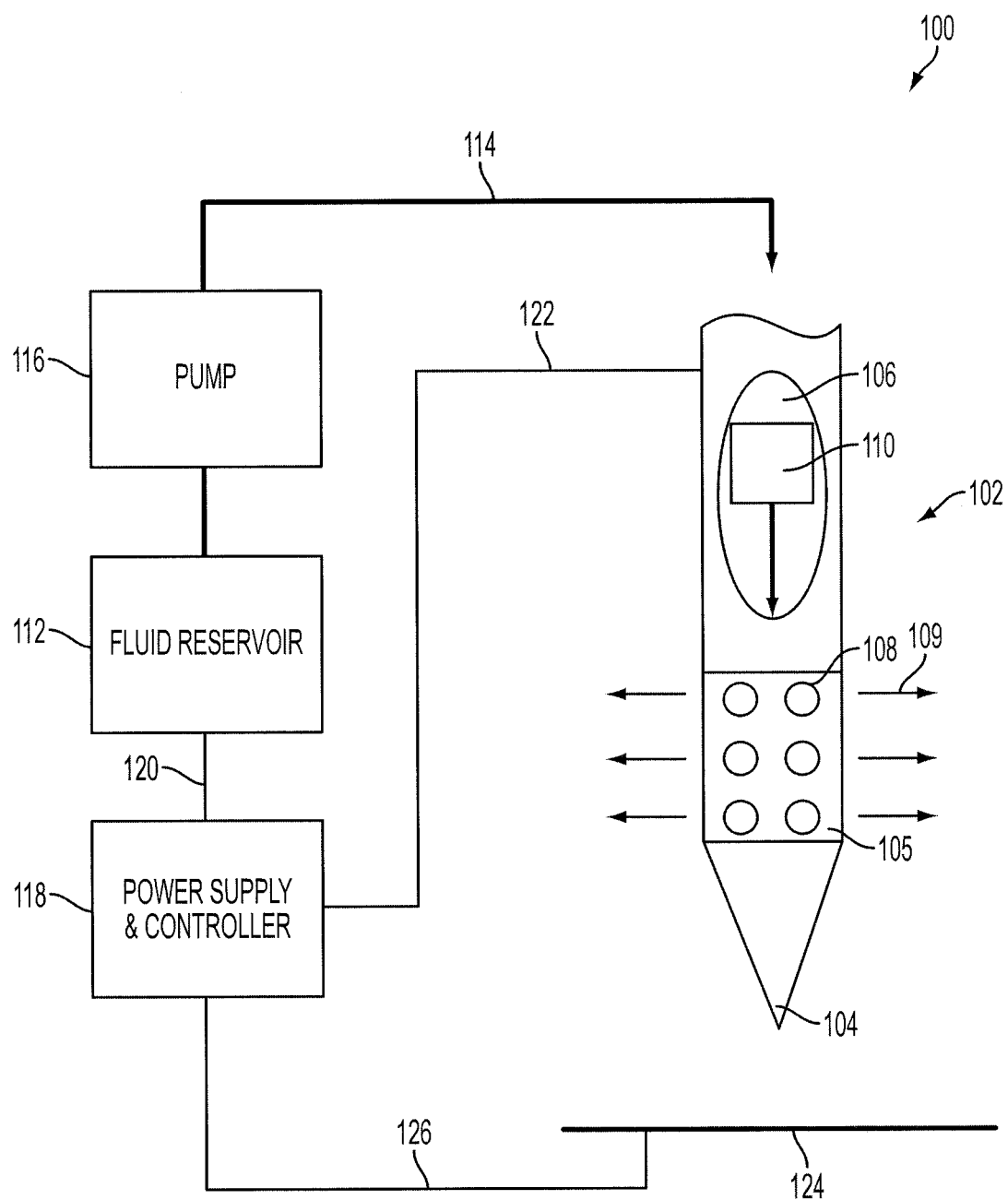
FIG. 1 is a diagram of one embodiment of a fluid enhanced ablation system.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to the use of "saline" as opposed to another fluid unless explicitly indicated. Other fluids can typically be used in a similar manner.

Fluid Enhanced Ablation Systems

The present invention is generally directed to heater elements used in fluid enhanced ablation devices. Fluid enhanced ablation, as mentioned above, is defined by passing a fluid into tissue while delivering therapeutic energy from an ablation element. The delivery of therapeutic energy into tissue causes hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

Fluid enhanced ablation, such as the SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. Delivering heated fluid enhances the ablation treatment because the fluid flow through the extracellular space of the treatment tissue can increase the heat transfer through the tissue by more than a factor of twenty. The flowing heated fluid therefore convects thermal energy from the ablation energy source further into the target tissue. In addition, the fact that the fluid is heated to a therapeutic temperature increases the amount of energy that can be imparted into the tissue. Finally, the fluid can also serve to constantly hydrate the tissue and prevent any charring and associated impedance rise, as described in more detail below.

Figure 2:
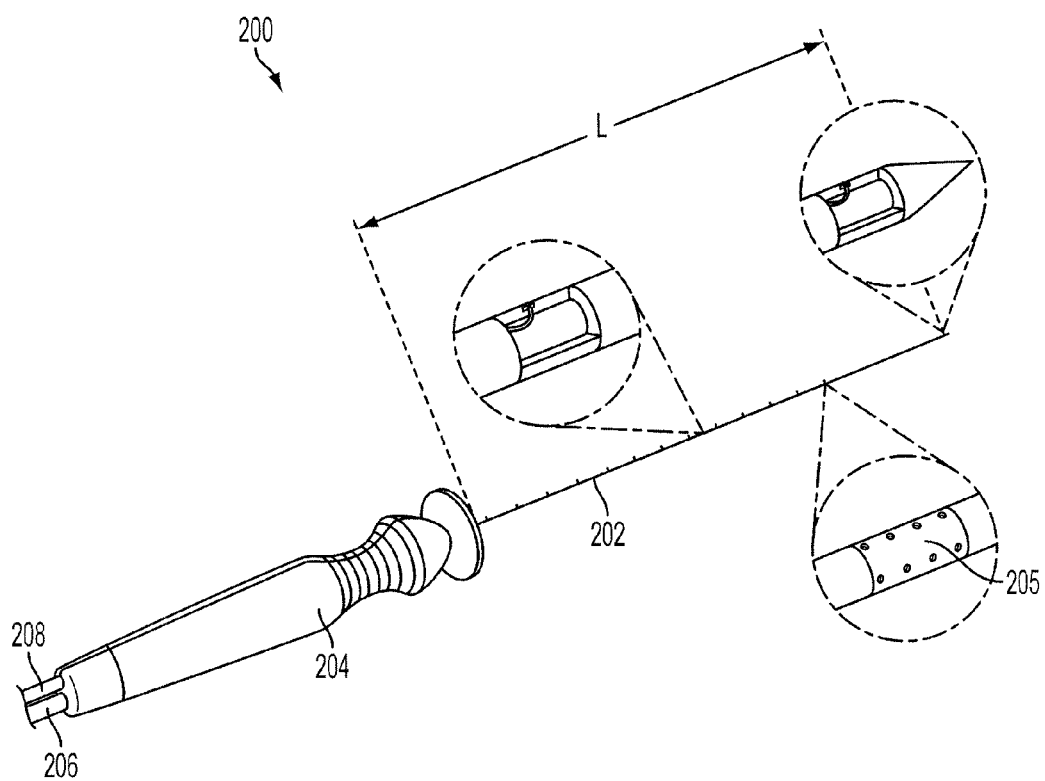
FIG. 2 is a perspective view of one embodiment of a medical device having an elongate body for use in fluid enhanced ablation.

FIG. 1 illustrates a diagram of one exemplary fluid ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 mm to about 1.65 mm), and having a length L (e.g., as shown in FIG. 2) that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated with 1.5 mil of the fluoropolymer Xylan™ 8840. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body.

In other embodiments, the electrode can be formed from a variety of other materials suitable for conducting current.

Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 105 or other ablation element can include one or more outlet ports 108 that are configured to deliver fluid from an inner lumen 106 extending through the elongate body 102 into surrounding tissue (as shown by arrows 109). Alternatively, the electrode 105 can be positioned near one or more outlet ports 108 formed in the elongate body 102. In many embodiments, it can be desirable to position the electrode adjacent to the one or more outlet ports to maximize the effect of the flowing fluid on the therapy. The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109 in FIG. 1, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. By way of example, in one embodiment, twenty-four equally-spaced outlet ports 108 having a diameter of about 0.4 mm can be created around the circumference of the electrode 105 using Electrical Discharge Machining (EDM). One skilled in the art will appreciate that additional manufacturing methods are available to create the outlet ports 108. In addition, in some embodiments, the outlet ports can be disposed along a portion of the elongate body adjacent to the electrode, rather than being disposed in the electrode itself.

The inner lumen 106 that communicates with the outlet ports 108 can also house a heating assembly 110 configured to heat fluid as it passes through the inner lumen 106 just prior to being introduced into tissue. Furthermore, the portion of the elongate body located distal to the electrode 105 or other ablation element can be solid or filled such that the inner lumen 106 terminates at the distal end of the electrode 105. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Fluid can be supplied to the inner lumen 106 and heating assembly 110 from a fluid reservoir 112. The fluid reservoir 112 can be connected to the inner lumen 106 via a fluid conduit 114. The fluid conduit 114 can be, for example, a length of flexible plastic tubing. The fluid conduit 114 can also be a rigid tube, or a combination of rigid and flexible tubing.

Fluid can be urged from the fluid reservoir 112 into the inner lumen 106 by a pump 116. The pump 116 can be a syringe-type pump that produces a fixed volume flow with advancement of a plunger (not shown). An example of such a pump is a Model 74900 sold by Cole-Palmer Corporation of Chicago, Ill. Other types of pumps, such as a diaphragm pump, may also be employed.

The pump 116 can be controlled by a power supply and controller 118. The power supply and controller 118 can deliver electrical control signals to the pump 116 to cause the pump to produce a desired flow rate of fluid. The power supply and controller 118 can be connected to the pump 116 via an electrical connection 120. The power supply and controller 118 can also be electrically connected to the elongate body 102 via connection 122, and to a collector electrode 124 via connection 126. In addition, the power supply and controller 118 can be connected to the heating assembly 110 through a similar electrical connection, as described below.

The collector electrode 124 can have a variety of forms. For example, the collector electrode 124 can be a large electrode located outside a patient's body. In other embodiments, the collector electrode 124 can be a return electrode located elsewhere along the elongate body 102, or it can be located on a second elongate body introduced into a patient's body near the treatment site.

In operation, the power supply and controller 118 can drive the delivery of fluid into target tissue at a desired flow rate, the heating of the fluid to a desired therapeutic temperature, and the delivery of therapeutic ablative energy via the one or more ablation elements, such as electrode 105. To do so, the power supply and controller 118 can itself comprise a number of components for generating, regulating, and delivering required electrical control and therapeutic energy signals. For example, the power supply and controller 118 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 122 and the elongate body 102 such that RF energy is passed between the emitter electrode 105 and the collector electrode 124 that can be located remotely on a patient's body. In embodiments in which the elongate body is formed from non-conductive material, the one or more electrical connections 122 can extend through the inner lumen of the elongate body or along its outer surface to deliver current to the emitter electrode 105. The passage of RF energy between the ablation element and the collector electrode 124 can heat the tissue surrounding the elongate body 102 due to the inherent electrical resistivity of the tissue. The power supply and controller 118 can also include a directional coupler to feed a portion of the one or more RF signals to, for example, a power monitor to permit adjustment of the RF signal power to a desired treatment level.

The elongate body 102 illustrated in FIG. 1 can be configured for insertion into a patient's body in a variety of manners. FIG. 2 illustrates one embodiment of a medical device 200 having an elongate body 202 coupled to a distal end thereof and configured for laparoscopic or direct insertion into a target area of tissue. In addition to the elongate body 202, the device 200 can include a handle 204 to allow an operator to manipulate the device. The handle 204 can include one or more electrical connections 206 that connect various components of the elongate body (e.g., the heating assembly and ablation element 205) to, for example, the power supply and controller 118 described above. The handle 204 can also include at least one fluid conduit 208 for connecting a fluid source to the device 200.

While device 200 is one exemplary embodiment of a medical device that can be adapted for use in fluid enhanced ablation, a number of other devices can also be employed. For example, a very small elongate body can be required in treating cardiac dysrhythmias, such as ventricular tachycardia. In such a case, an appropriately sized elongate body can be, for example, disposed at a distal end of a catheter configured for insertion into the heart via the circulatory system. In one embodiment, a stainless steel needle body between about 20- and about 25-gauge (i.e., an outer diameter of about 0.5 mm to about 0.9 mm) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters).

Therapeutic Treatment Using Fluid Enhanced Ablation

Ablation generally involves the application of high or low temperatures to cause the selective necrosis and/or removal of tissue. There is a known time-temperature relationship in the thermal destruction of tissue accomplished by ablation. A threshold temperature for causing irreversible thermal damage to tissue is generally accepted to be about 41° Celsius (C). It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as:

$$t_{eq.43° C.} = \int R^{(T(t)-43°)} dt \quad (1)$$

where T is the tissue temperature and R is a unit-less indicator of therapeutic efficiency in a range between 0 and 5 (typically 2 for temperatures greater than or equal to 43° C., zero for temperatures below 41° C., and 4 for temperatures between 41 and 43° C.), as described in Sapareto S. A. and W. C. Dewey, *Int. J. Rad. Onc. Biol. Phys.* 10(6):787-800 (1984). This equation and parameter set represents just one example of the many known methods for computing a thermal dose, and any of methodology can be employed with the methods and devices of the present invention. Using equation (1) above, thermal doses in the range of $t_{eq.43° C.}$=20 minutes to 1 hour are generally accepted as therapeutic although there is some thought that the dose required to kill tissue is dependent on the type of tissue. Thus, therapeutic temperature may refer to any temperature in excess of 41° C., but the delivered dose and, ultimately, the therapeutic effect are determined by the temporal history of temperature (i.e., the amount of heating the tissue has previously endured), the type of tissue being heated, and equation (1). For example, Nath, S. and Haines, D. E., *Prog. Card. Dis.* 37(4):185-205 (1995) (Nath et al.) suggest a temperature of 50° C. for one minute as therapeutic, which is an equivalent time at 43° C. of 128 minutes with R=2. In addition, for maximum efficiency, the therapeutic temperature should be uniform throughout the tissue being treated so that the thermal dose is uniformly delivered.

Figure 3:
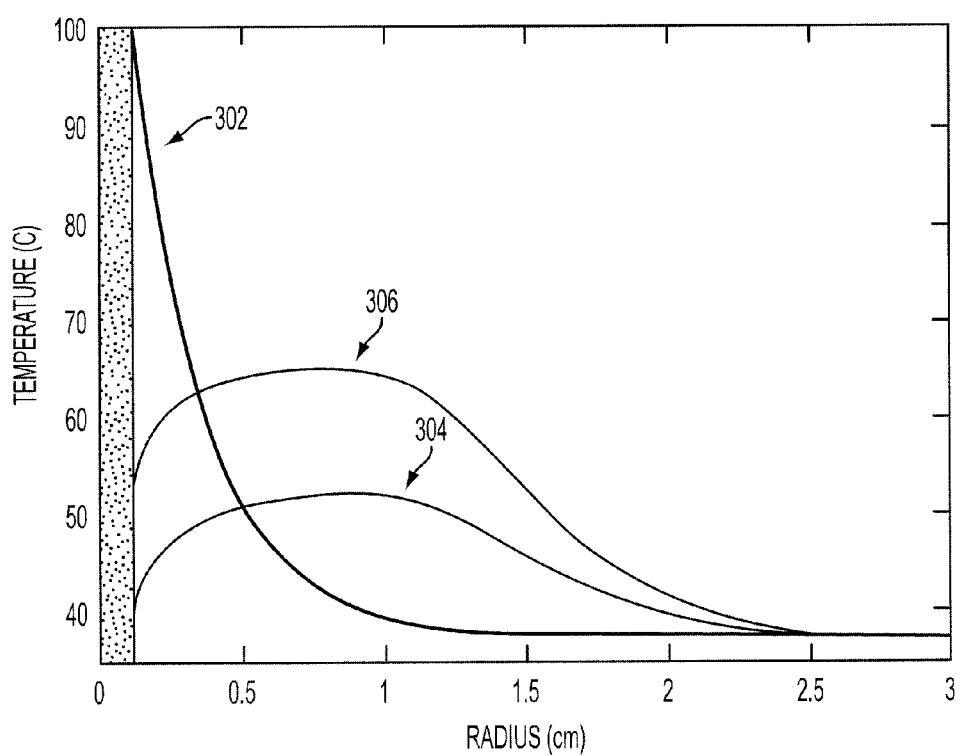
FIG. 3 is a graphical representation of simulated heating profiles for various forms of ablation.

FIG. 3 illustrates the performance profiles of several ablation techniques by showing a simulated temperature profile achieved as a function of distance from an ablation element, such as electrode 105. The first profile 302 illustrates the performance of RF ablation without the use of fluid enhancement. As shown in the figure, the temperature of the tissue falls very sharply with distance from the electrode. This means that within 10 mm of the ablation element the temperature of the tissue is still approximately body temperature (37° C.), far below the therapeutic temperature of 50° C. discussed above. Furthermore, very close to the ablation element the temperature is very high, meaning that the tissue will more quickly desiccate, or dry up, and char. Once this happens, the impedance of the tissue rises dramatically, making it difficult to pass energy to tissue farther away from the ablation element.

A second tissue temperature profile 304 is associated with a second prior art system similar to that described in U.S. Pat. No. 5,431,649. In this second system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 304 is more uniform than profile 302, but the maximum temperature achieved anywhere is approximately 50° C. Thus, the temperature profile 304 exceeds the generally accepted tissue damaging temperature threshold specified for one minute of therapy in only a small portion of the tissue. As described above, such a small temperature increment requires significant treatment time to achieve any therapeutically meaningful results.

A third tissue temperature profile 306 is achieved using the teachings of the present invention. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 306 is both uniform and significantly above the 50° C. therapeutic threshold out to 15 mm from the electrode. Moreover, because the temperature is uniform within the volume, the thermal dose delivered is also uniform through the volume.

The uniform temperature profile seen in FIG. 3 can be achieved by the introduction of heated fluid into the target tissue during application of ablative energy. The fluid convects the heat deeper into the tissue, thereby reducing the charring and impedance change in tissue that occurs near the ablation element, as shown in profile 302. Further, because the fluid is heated to a therapeutic level, it does not act as a heat sink that draws down the temperature of the surrounding tissue, as seen in profile 304. Therefore, the concurrent application of RF energy and perfusion of heated saline solution into the tissue eliminates the desiccation and/or vaporization of tissue adjacent to the electrode, maintains the effective tissue impedance, and increases the thermal transport within the tissue being heated with RF energy. The total volume of tissue that can be heated to therapeutic temperatures, e.g., greater than 41° C., is thereby increased. For example, experimental testing has demonstrated that a volume of tissue having a diameter of approximately 8 cm (i.e., a spherical volume of approximately 156 cm$^3$) can be treated in 5 minutes using the fluid enhanced ablation techniques described herein. By comparison, conventional RF can only treat volumes having a diameter of approximately 3 cm (i.e., a spherical volume of approximately 14 cm$^3$) in the same 5-minute timespan.

In addition, fluid enhanced ablation devices according to the present invention have a greater number of parameters that can be varied to adjust the shape of the treatment profile according to the tissue being treated. For example, when using the SERF ablation technique, an operator or control system can modify parameters such as saline temperature (e.g., from about 40° C. to about 80° C.), saline flow rate (e.g., from about 0 ml/min to about 20 ml/min), RF power (e.g., from about 0 W to about 100 W), and duration of treatment (e.g., from about 0 min to about 10 min) to adjust the temperature profile 306. In addition, different electrode configurations can also be used to vary the treatment. For example, although the emitter electrode 105 illustrated in FIG. 1 is configured as a continuous cylindrical band adapted for a mono-polar current flow, the electrode can also be formed in other geometries, such as spherical or helical, that form a continuous surface area, or the electrode may have a plurality of discrete portions. The electrodes may also be configured for bipolar operation, in which one electrode (or a portion of an electrode) acts as a cathode and another electrode (or portion thereof) acts as an anode.

A preferred fluid for use in the SERF ablation technique is sterile normal saline solution (defined as a salt-containing solution). However, other liquids may be used, including Ringer's solution, or concentrated saline solution. A fluid can be selected to provide the desired therapeutic and physical properties when applied to the target tissue and a sterile fluid is recommended to guard against infection of the tissue.

Dual-Wire Heating Assembly

Figure 4:
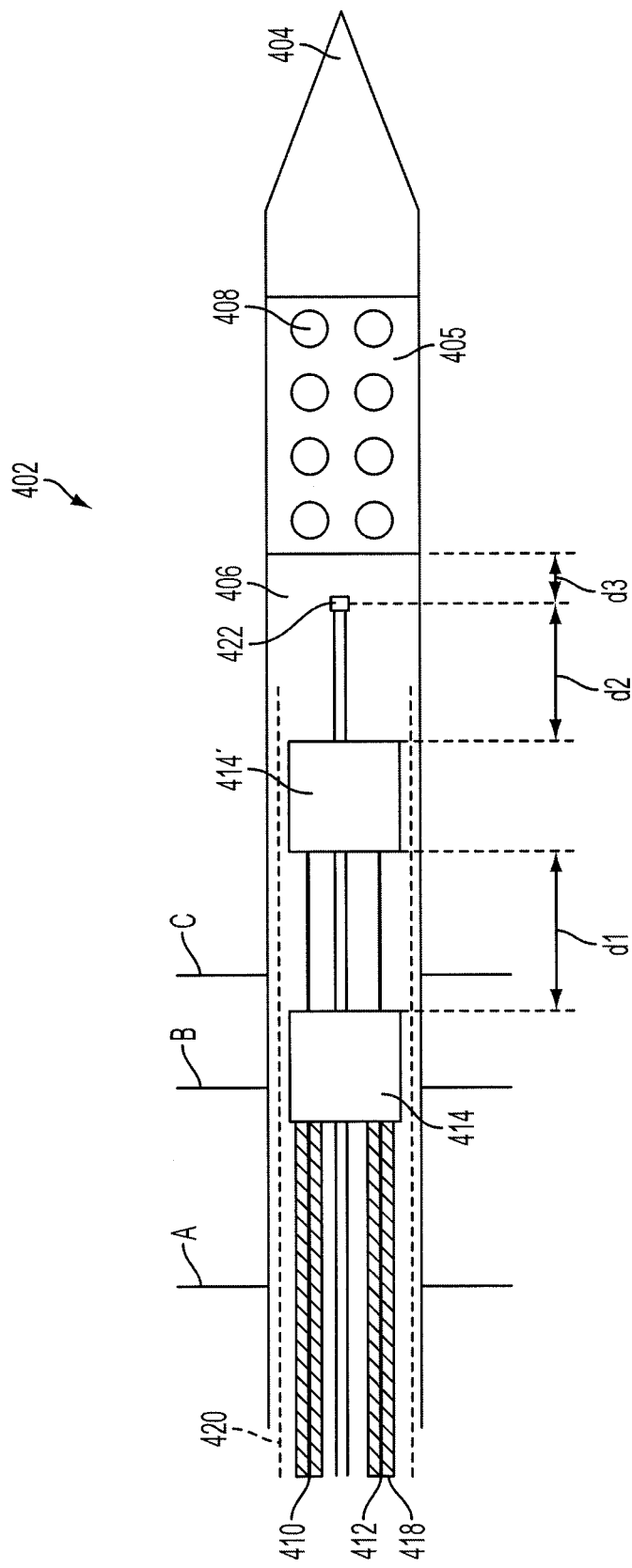
FIG. 4 is a diagram of one embodiment of an elongate body having a dual-wire heating assembly.

As described above, saline or another fluid flowing within an inner lumen of an elongate body can be heated to a therapeutic temperature by a heating assembly disposed within the inner lumen. FIG. 4 illustrates one embodiment of such an assembly. An elongate body 402 having a proximal end and a pointed distal end 404 includes an inner lumen 406. The elongate body 402 can also include at least one ablation element, such as emitter electrode 405, that is configured to deliver RF energy to tissue surrounding the elongate body 402. The electrode 405 also includes one or more outlet ports 408 configured to deliver fluid from the inner lumen 406 into surrounding tissue.

Disposed within the inner lumen 406 is a heating assembly that includes two wires 410, 412 that are suspended a distance apart by one or more spacers 414, 414'. The wires 410, 412 can be connected to a power source such that electrical energy can be passed between the wires through the fluid flowing in the inner lumen 406. The passage of electrical (e.g., RF) energy through the fluid in the inner lumen 406 can cause the fluid to increase in temperature due to the natural electrical resistivity of the fluid, similar to the mechanism discussed above by which tissue surrounding the elongate body can be heated using RF energy. The wires 410, 412 can be formed from any conductive material, similar to the materials discussed above in connection with the electrode 105. In one embodiment, however, the wires 410, 412 can be formed from silver wire and can have an exposed chlorided surface between or adjacent to the spacers 414, 414'. As discussed above, these materials can participate in an ion exchange process that minimizes the voltage drop across the wire/fluid interface and prevents excessive heating of the surrounding fluid.

In order to effectively pass energy through the fluid flowing within the inner lumen 406, in an exemplary embodiment, the wires 410, 412 (or at least the exposed portion of the wires) are prevented from coming into contact with one another, as this can cause an electrical short. The spacers 414, 414' can have a variety of configurations, but in one embodiment they can be disc-shaped members that maintain the wires 410, 412 in a fixed geometric relationship with one another, i.e., at a fixed distance apart and at a fixed orientation in space relative to one another. In some embodiments, the wires 410, 412 are exposed for only a short distance located just proximal of the electrode 405 and outlet ports 408. As shown in FIG. 4, the wires can be exposed for a distance $d_1$ between the two spacers 414, 414' that are positioned at a proximal and a distal end of a distal portion of the wires. Proximal to the spacer 414, the wires 410, 412 can be covered in an electrically insulating material 418 to prevent the passage of electrical energy therebetween. In addition, the wires 410, 412 can also be prevented from directly contacting the elongate body 402, as an electrical short can result from both of the wires 410, 412 simultaneously contacting the electrically conductive elongate body. Accordingly, in some embodiments, the elongate body 402 can be lined with an insulating material 420, such as a plastic tube, liner, or coating disposed on the inner walls of the elongate body 402.

Furthermore, the spacers 414, 414' can be configured to occupy the entire inner diameter of the elongate body 402, or can be configured to float within the elongate body's inner lumen 406 by having a maximum outer diameter that is less than a diameter of the inner lumen 406. This configuration can allow the spacers 414, 414' to move radially relative to the central longitudinal axis of the inner lumen 406. The position of the spacers 414, 414' can be fixed by configuring the spacers to have an interference fit between the inner walls of the elongate body 402 or insulating material 420, by adhering the spacers 414, 414' to a portion of the elongate body using, for example, an adhesive, or by using spokes, arms, or other surface features that extend radially outward from the spacers and engage the inner wall of the inner lumen. Accordingly, the spacers 414, 414' can also be effective to maintain the wires 410, 412 in a substantially fixed geometric relationship with the elongate body 402.

The number of spacers 414 required to maintain the wires 410, 412 in relation with each other and/or the elongate body 402 can vary according to a number of factors including the length of the exposed wire section, the inner diameter of the elongate body 402, the diameter of the wires 410, 412, the stiffness of the wires used, and the size of the elongate body 402. In the embodiment illustrated in FIG. 4, two spacers 414, 414' are used to hold the wires 410, 412 apart over a distance $d_1$. The distance $d_1$ can vary and, in one embodiment, can be about 5 mm. Furthermore, the thickness of the spacers 414 can also be adjusted according to the mechanical demands required by the particular configuration of the elongate body 402 and wires 410, 412.

The inner lumen 406 can also house one or more temperature sensors to monitor and assist in controlling the heating of fluid flowing within the inner lumen. The embodiment illustrated in FIG. 4 includes a chromel-constantan fine-wire thermocouple configured to float in the fluid distal of the spacer 414' by a distance $d_2$. One skilled in the art will appreciate that thermocouples are just one example of temperature sensors that can be employed to measure the temperature of the flowing fluid and that a variety of sensors, including thermistors and diodes, can also be used. Further, distance $d_2$ can vary and, in one embodiment, it can be about 10 mm. The thermocouple 422 can also be disposed a distance $d_3$ proximal to the electrode 405 and outlet ports 408. While this distance can vary as well, in one embodiment, the distance $d_3$ is about 2 mm. The distances $d_1$, $d_2$, and $d_3$ (and the corresponding positions of the spacers 414, 414') can be chosen to allow for sufficient heating of fluid flowing in the inner lumen 406, as well as to allow sufficient mixing of the heated fluid prior to flowing through outlet ports 408 so as to assure that the fluid being injected into tissue surrounding the elongate body 402 has a uniform temperature. However, the distances $d_2$ and $d_3$ should be minimized such that heating of the fluid flowing within the inner lumen 406 occurs as close to the outlet ports 408 as possible. This configuration minimizes the thermal losses and unintentional environmental heating associated with transporting heated fluids from remote locations within a patient's body.

Figure 5C:
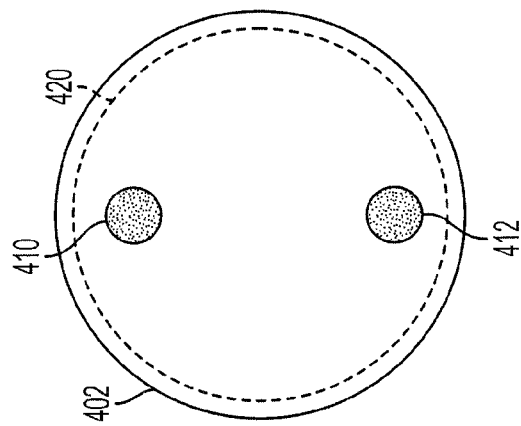
FIG. 5C is a cross-sectional diagram of the elongate body of FIG. 4 at a location between the spacer elements.
Figure 5B:
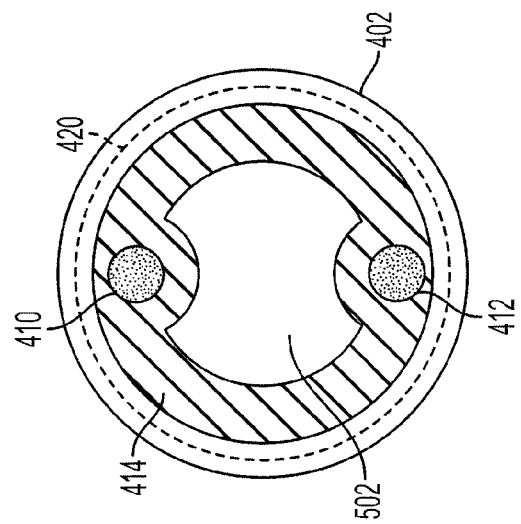
FIG. 5B is a cross-sectional diagram of the elongate body of FIG. 4 at a location of a spacer element.
Figure 5A:
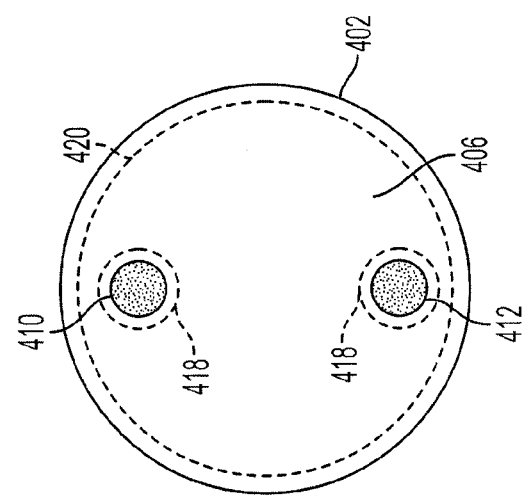
FIG. 5A is a cross-sectional diagram of the elongate body of FIG. 4 proximal to a spacer element.

FIGS. 5A-5C illustrate the device of FIG. 4 in cross-section at locations A, B, and C, respectively. FIG. 5A illustrates the elongate body 402 in a portion proximal to the heating assembly. As shown in the figure, the elongate body 402 can be lined with an insulating material 420, and wires 410, 412 can also each be coated with an insulating material 418. One skilled in the art will appreciate that the insulating material 420 is not necessary where the wires 410, 412 are coated with insulating material 418. Therefore, the insulating material 420 can be present along the entire length of the elongate body, as shown in FIG. 5A, or can be positioned only along portions where the wires 410, 412 are exposed, as described below with respect to FIG. 5C. Further, as is explained in more detail below, insulating material need not be present at all in some embodiments due to the isolation of the separate power sources that connect to the wires 410, 412 and the ablation element 405. Throughout any portion of the elongate body in which the wires 410, 412 are coated in insulating material 418, the wires 410, 412 can be allowed to float freely in the inner lumen 406. Alternatively, one or more spacers 414 can be disposed along the length of the elongate body 402 to maintain the wires 410, 412 in position with respect to each other and the elongate body 402.

FIG. 5B illustrates the elongate body 402 in a portion having a spacer 414. Visible in the figure is the elongate body 402, the inner lumen 406, the insulating material 420, the spacer 414, and the wires 410, 412. From this view, spacer 414 is revealed as a disc or cylindrical member having two bores and at least one central lumen 502 through which fluid can flow to bypass the spacer 414 in the event that the spacer occupies the entire inner diameter of the elongate body 402. In other embodiments, particularly those in which the spacer does not occupy the entire inner diameter of the elongate body 402 such that fluid can flow around the spacer, the spacer need not have a central lumen. In one embodiment, the spacers 414, 414' can be formed from a single 3-lumen extruded tube that is subsequently cut into individual spacers of a desired thickness. The wires 410, 412 can be threaded through the two bores formed in the spacer 414 (shown in FIG. 5B as co-located with the wires 410, 412) and held in place by, for example, an interference fit or an epoxy adhesive.

FIG. 5C shows the elongate body 402 in a portion adjacent to the spacer 414 and between spacers 414, 414'. The wires 410, 412 are exposed in this portion and configured to heat the fluid flowing therebetween. In such a location within the elongate body 402, the wires 410, 412 are free of any insulation and prevented from contacting the elongate body 402 by the insulating material 420 and the restraining forces of the adjacent spacers 414, 414'.

Figure 6:
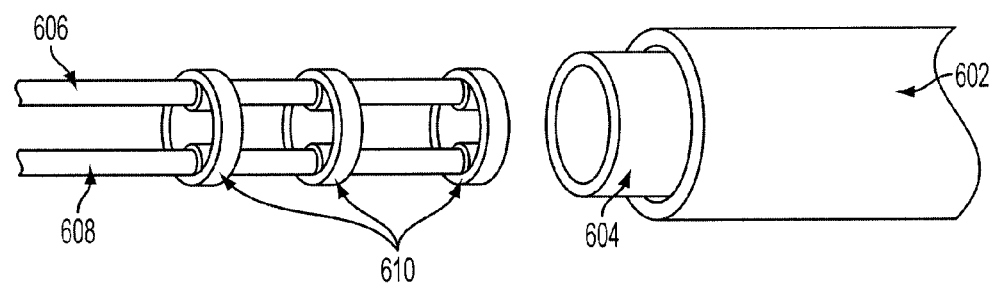
FIG. 6 is an exploded perspective view of one embodiment of an elongate body having a dual-wire heating assembly.

FIG. 6 illustrates an exploded view of a heating assembly similar to that of FIGS. 4 and 5A-5C. As shown in the figure, an inner lumen of a stainless steel elongate body 602 can be lined with an insulating material 604, such as a plastic tube. A heating assembly comprising two wires 606, 608 and one or more spacers 610 can then be placed within the inner lumen such that the wires 606, 608 are prevented from coming into direct contact with each other or the elongate body 602.

Figure 7:
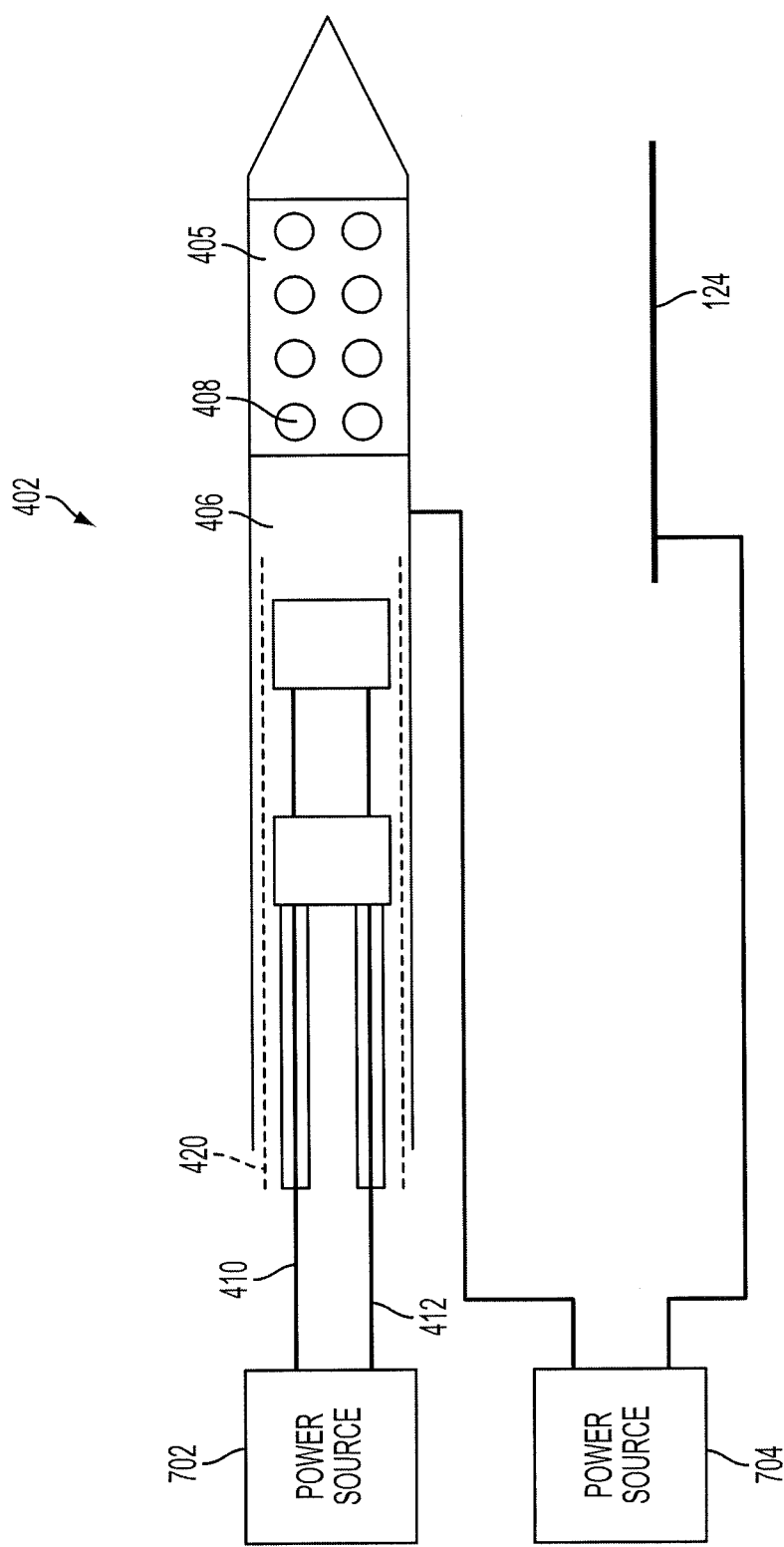
FIG. 7 is a diagram of one embodiment of an electrical circuit for driving the elongate body and heating assembly of FIG. 4.

FIG. 7 illustrates an exemplary electrical circuit for delivering RF energy to both tissue surrounding the elongate body 402 and fluid flowing through the inner lumen 406 of the elongate body 402. In the illustrated embodiment, two separate power sources 702, 704 are utilized to deliver electrical energy including, for example, RF energy. The power source 702 can be connected to the two wires 410, 412 running through the inner lumen 406 of the elongate body 402. By passing electrical current through the wires, energy can be transmitted through the fluid flowing within the inner lumen 406 between the exposed portions of the wires 410, 412.

The power source 704 can be connected to both the elongate body 402 and a collector electrode 124. The collector electrode can be located remotely on a patient's body, for example, placed under a patient's back on an operating table. As discussed above, in other embodiments, the collector electrode 124 can be co-located on the elongate body 402 or it can be located on a second elongate body positioned nearby the elongate body 402. One skilled in the art will appreciate that positioning the collector electrode 124 on the elongate body 402 requires isolating the emitter electrode 405 from the collector electrode. This can be accomplished in a variety of manners including, for example, by forming the elongate body 402 from a non-conducting material and placing the two electrodes on the surface of the elongate body 402. In such an embodiment, the power source 704 can be connected to the two electrodes by any suitable electrical connection, such as wires extending through the inner lumen of the elongate body 402 or along its outer surface.

Referring back to the figure, the power source 704 can deliver RF energy from the electrode 405 to the collector electrode 124 by passing electrical current through the elongate body 402. The two power sources 702, 704 do not share a common electrical ground and therefore remain electrically isolated from one another. This ensures that power from the source 702 heats only saline flowing within the elongate body 402, while power from the source 704 heats only tissue surrounding the elongate body 402. The spacers and insulating materials discussed above are utilized to prevent a short between the two wires 410, 412 that can result from the wires touching each other or simultaneously contacting the elongate body 402. One skilled in the art will appreciate that a variety of combinations of spacers and insulating materials covering the wires and/or the inner walls of the elongate body can be used to prevent such an electrical short circuit.

In an exemplary embodiment, as saline solution is pumped through the elongate body's inner lumen 406, the saline can be heated above body temperature by the power source 702, preferably to between about 50° C. and about 70° C. This can be accomplished by delivering RF energy to the fluid within the inner lumen 406 via the wires 410, 412. For example, typical fluid enhanced ablation therapy operating parameters involve the application of 20 volts or more to the wires 410, 412. In some embodiments, the applied voltage can go as high as 120 volts and, in some embodiments, can be about 30 volts (e.g., 31.25 volts in one embodiment). The heated, flowing saline solution can be subsequently injected into tissue surrounding the elongate body 402 via the outlet ports 408 at a variety of flow rates. For example, in some embodiments fluid can be ejected from the elongate body 402 at a flow rate of about 10 ml/min. The delivery of heated fluid can be done independently or in conjunction with the delivery of ablative energy from the power source 704. The operating parameters of fluid enhanced ablation therapy can vary according to a number of factors, including the desired therapeutic effect, the geometry and tissue properties of the treatment volume, etc. By way of example, in one embodiment ablation therapy conducted in a patient's liver can heat saline to 50° C. using 40 watts of power and deliver the saline at 10 ml/min for about 5 minutes. By way of further example, ablation therapy using these same parameters can be delivered for only about 90 seconds when treating cardiac tissue. While the particular properties of the intended treatment site will ultimately govern the selected operating parameters, fluid enhanced ablation therapy typically involves the delivery of saline at a rate between about 0 and about 20 ml/min. The saline is typically heated to between about 50° C. and 80° C. using up to 80 watts of power and up to 120 volts. Fluid heated according to these exemplary operating parameters can be combined with electrical energy delivered directly to the tissue to conduct ablation therapy. In some embodiments, up to 100 watts of power can be applied to the tissue from, for example, an emitter electrode.

Single-Wire Heating Assembly

Figure 8:
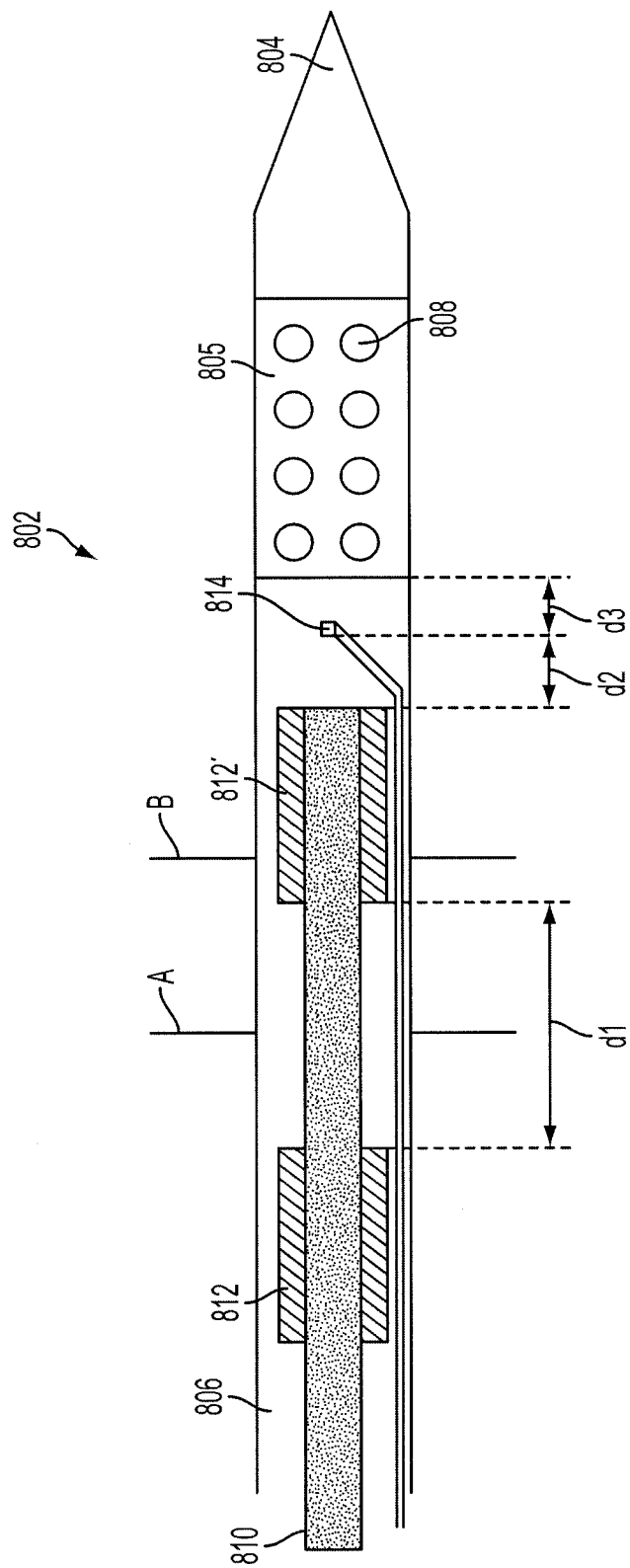
FIG. 8 is a diagram of one embodiment of an elongate body having a single-wire heating assembly.

A second embodiment of the heating assembly 110 is illustrated in FIG. 8. This embodiment uses a single wire in combination with a conductive elongate body or a conductive tube placed within the elongate body to deliver RF energy to fluid flowing within an inner lumen of the elongate body. This heater design can have advantages in embodiments where small elongate bodies are used to access, for example, areas of a patient's heart in treating cardiac dysrhythmias such as ventricular tachycardia. Further, this configuration can provide more uniform heating of fluid flowing through the inner lumen of the elongate body, as discussed below. Still further, one skilled in the art will appreciate that the dual-wire and single-wire assemblies can include any combination of features disclosed herein with respect to each embodiment.

As shown in the figure, the elongate body 802 includes a proximal end and a pointed distal tip 804, and includes at least one ablation element, such as electrode 805, disposed along the length thereof. The elongate body 802 also includes an inner lumen 806 that is in fluid communication with one or more outlet ports 808 formed in the electrode 805. The elongate body 802 can be formed from similar materials as the elongate body 102 discussed above, i.e., electrically conductive materials capable of passing current from a power source to the electrode 805.

Disposed within the inner lumen 806 of the elongate body 802 can be a wire 810 configured to deliver RF energy to fluid flowing within the inner lumen via an exposed portion extending a distance $d_1$ between two spacer elements 812, 812'. The spacer elements 812, 812' can hold the wire 810 in a substantially fixed geometric relationship with the elongate body 802 and can be formed from an electrically insulating material such as a plastic. By maintaining a substantially fixed geometric relationship, the spacers 812, 812' can prevent the exposed portion of the wire 810 from directly contacting the elongate body 802 and causing an electrical short. Note that the wire 810 can be coated in an insulating material (not shown) similar to insulating material 418 along any portions located proximal to the spacer 812.

The distance $d_1$ separating the spacers 812, 812' can vary according to the desired heating capacity, power source, wire diameter, and elongate body size in a particular embodiment. In one embodiment, the elongate body can be a 25-gauge thin-walled needle having an inner diameter of about 0.4 mm. A wire having an outer diameter less than the inner diameter of the elongate body can have an exposed portion where $d_1$ can be about 2 mm. In one embodiment, the wire can have an outer diameter of about 0.125 mm. The exposed portion of the wire 810 can be located just proximal to the electrode 805 and its outlet ports 808, but some distance should be left separating the components so that fluid being heated by the wire 810 has time to sufficiently mix and reach a more uniform temperature before being introduced into tissue surrounding the elongate body.

Similar to the first embodiment discussed above, one or more temperature sensors 814 can also be disposed within the inner lumen 806 to aid in controlling the heating of fluid flowing through the inner lumen. For example, a temperature sensor 814 can be positioned between the distal end of the wire 810 and the proximal end of the electrode 805. That is, the temperature sensor 814 can be positioned a distance $d_2$ beyond the distal end of the wire 810, and a distance $d_3$ before the proximal end of the electrode 805. In some embodiments, the distance $d_2$ can be about 1 mm and the distance $d_3$ can be nearly 0 mm. The temperature sensor can be any of a variety of sensors, and in some embodiments can be a fine-wire chromel-constantan thermocouple known in the art.

Figure 9A:
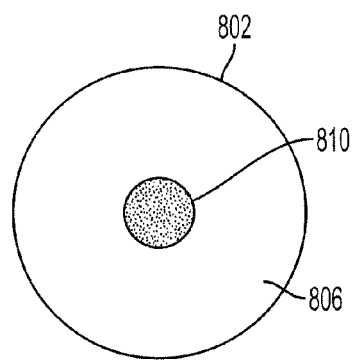
FIG. 9A is a cross-sectional diagram of the elongate body of FIG. 8 at a location adjacent to a spacer element.
Figure 9B:
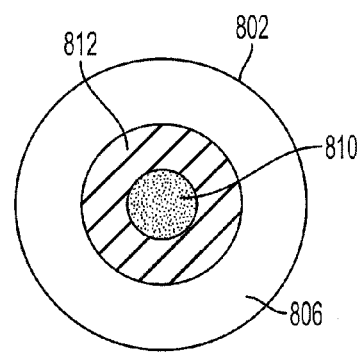
FIG. 9B is a cross-sectional diagram of the elongate body of FIG. 8 at a location of a spacer element.

FIGS. 9A and 9B illustrate the elongate body of FIG. 8 in cross-section at locations A and B, respectively. As shown in FIG. 9A, when the wire 810 is exposed between the spacers 812, 812', it is free to pass electrical energy to the elongate body 802, thereby heating any fluid in the inner lumen 806. Of note is the fact that the elongate body 802 is not lined with an insulating material, as described above. Rather, the elongate body 802 in this embodiment serves as the second electrode to receive energy from the wire 810. However, in some embodiments the elongate body 802 can be lined with an insulating material proximal to the spacer 812.

FIG. 9B illustrates the elongate body at a position in which the wire 810 is protected from contacting the elongate body 802 by a spacer 812. The spacer 812 can be capable of maintaining the wire 810 in a position substantially coaxial with a longitudinal axis of the elongate body. As shown in the figure, the spacer 812 need not occupy the entire diameter of the inner lumen 806. Rather, the spacer 812 can be formed in a variety of sizes and, in some embodiments, may occupy substantially all of the available space in the inner lumen 806 while, in other embodiments, it may be significantly smaller. In embodiments in which the spacer 812 does occupy substantially all of the inner lumen 806, it may be necessary to form the spacer with one or more passages such that fluid can flow around the spacer, similar to the central lumen 502 of the spacer 414 described above. One skilled in the art will appreciate that the spacer 812 can be formed as an extruded tube, similar to the spacer 414. Such an extrusion can be formed with one or more lumens that can serve as passageways for fluid. In addition, the wire 810 can be coated in an insulating material over portions where energy transfer is undesirable. For example, the wire 810 can be coated with an insulating material over the portion of the wire extending proximally from the spacer 812.

Figure 10:
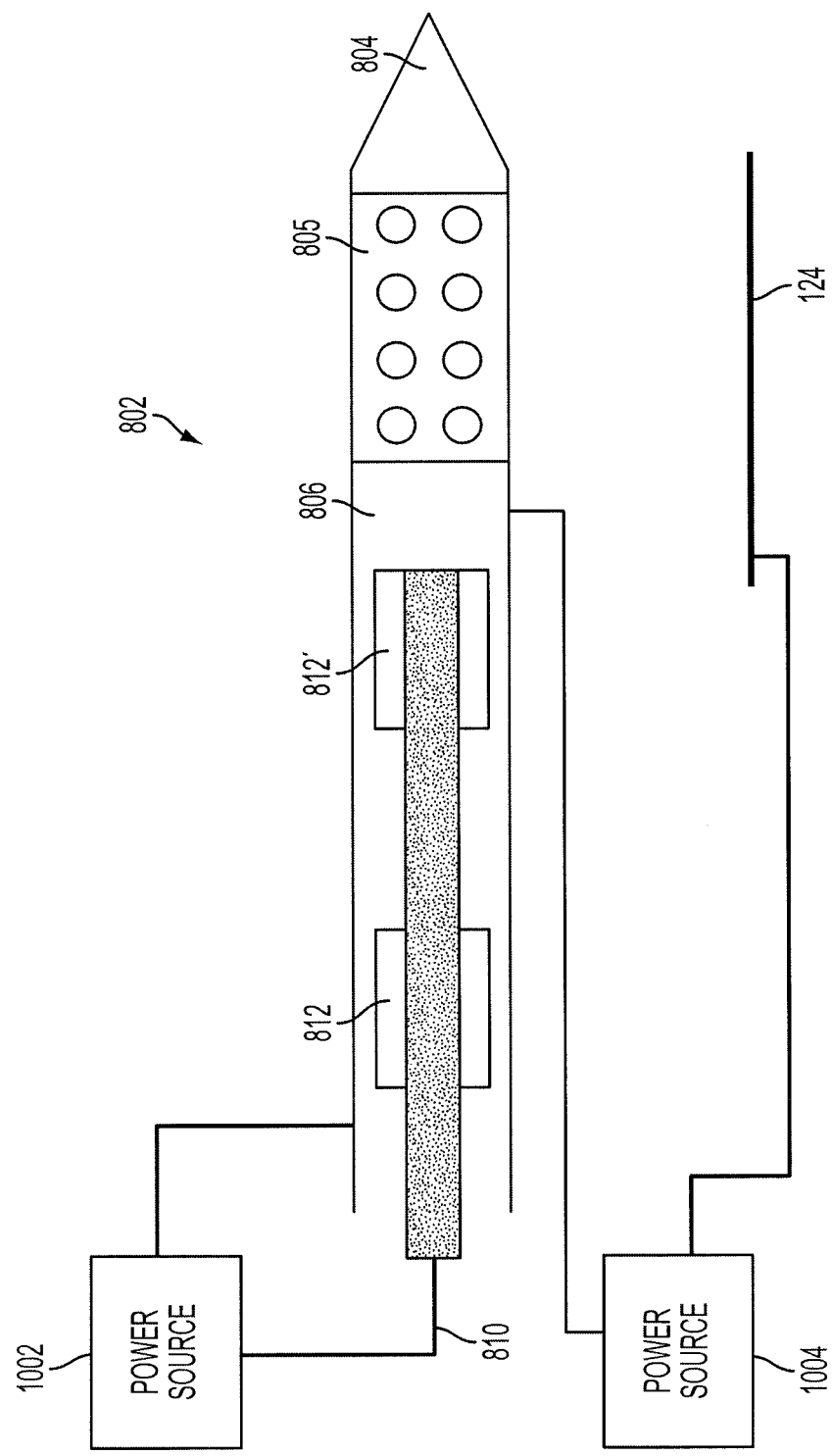
FIG. 10 is a diagram of one embodiment of an electrical circuit for driving the elongate body and heating assembly of FIG. 8.

FIG. 10 illustrates one embodiment of an electrical circuit for independently delivering RF energy to fluid flowing in the inner lumen 806 of the elongate body 802, as well as to tissue surrounding the elongate body. As shown in the figure, dual power sources 1002, 1004 are used to deliver energy to the fluid within the inner lumen 806 and the tissue surrounding the elongate body 802, similar to the circuit illustrated in FIG. 7. However, in the illustrated embodiment, the circuits formed by each power source 1002, 1004 share the elongate body 802 as a common electrode. In other words, power source 1002, which is configured to deliver RF energy to fluid flowing within the inner lumen 806, is connected to the wire 810 disposed within the inner lumen 806 and to the elongate body 802 itself. The elongate body 802, then, serves as an electrode for the power source 1002. The power source 1004, on the other hand, is connected to the elongate body 802 and the collector electrode 124. Accordingly, the power source 1004 can deliver RF energy from the electrode 805 into tissue surrounding the elongate body 802. As a result of the fact that the two power sources 1002, 1004 are only connected via the elongate body 802 (i.e., only connected at a single point without a return connection), the power sources are able to operate independently and simultaneously without any current flowing therebetween.

FIGS. 11A, 11B, and 12 illustrate alternative embodiments of the spacer 812. As described above, the spacer 812 can be formed as an extrusion of an insulating material, such as a polymer material, that can subsequently be affixed to the wire 810 using, for example, overjacketing extrusion, pressure tooling or using an adhesive. The spacer 812 can have a cylindrical shape to match the cylindrical shape of the inner lumen 806 and, in embodiments in which a non-cylindrical elongate body is used, the spacer 812 can be formed into any shape corresponding to the inner lumen 806. The spacer 812 can, however, assume other configurations as well. For example, the spacer 812 can be formed as one or more features attached to the wire 810 along its length. FIG. 11A shows one embodiment of such a spacer. The conducting wire 1102 can have formed thereon a number of longitudinally extending protrusions or ridges 1104 that are formed from an insulating material. The protrusions 1104 act similarly to the spacer 812 and prevent the wire 1102 from directly contacting the elongate body 802. These protrusions, unlike the spacer 812, do not completely surround the wire 1102, so they can extend along the entire exposed portion of the wire 1102 without preventing the passage of electrical energy through fluid flowing over the wire. As a result, energy can be passed between the wire 1102 and the elongate body 802 along any desired length without requiring individual spacer elements to hold an exposed length of the wire (e.g., spacers 812, 812').

FIG. 11B illustrates a cross-sectional view of the wire 1102, more clearly showing the four protrusions 1104 formed thereon. One skilled in the art will appreciate that any number of protrusions or ridges may be formed around the circumference of the wire 1102, but the number should be sufficient to prevent direct electrical contact with the elongate body 802 while not completely enclosing the surface area of the wire 1102. Furthermore, the protrusions can be formed in a variety of sizes. For example, the protrusions may be formed with a height that reaches to the inner walls of the elongate body 802, thereby preventing the wire 1102 from moving within the inner lumen 806. In other embodiments, the protrusions may have a lesser height that allows the wire 1102 to move radially within the inner lumen 806 while preventing direct contact between an exposed portion of the wire and the inner walls of the elongate body 802.

The protrusions 1104 can be formed on the wire 1102 in a variety of manners. For example, the protrusions can be extruded and subsequently applied to the surface of the wire 1102. Alternatively, the wire can be formed with an insulating coating as known in the art, and the coating can be selectively removed through an ablation process such that only the protrusions 1104 of insulating material remain. Alternatively, the wire can be formed and then the insulating protrusions applied using overjacketing extrusion. In addition, the protrusions 1104 can be formed in a variety of shapes other than the longitudinally extending ridges shown in FIGS. 11A and 11B. For example, FIG. 12 illustrates an example of a wire 1202 that has an insulating material coating 1204 in the shape of an auger or corkscrew. Such a shape can be created using, for example, the selective ablation process described above to remove portions of an insulating coating formed over the wire 1202.

Design Advantages

The various embodiments of the heating assembly 110 described herein provide a number of advantages for fluid enhanced ablation systems. For example, the ability of the spacers to hold one or more wires in a substantially fixed geometric relationship with a second wire and/or the elongate body itself enables the reliable production of a fluid enhanced ablation device or system. This is because any power source utilized to deliver RF energy to fluid flowing within the inner lumen of an elongate body can be configured to effectively heat only a limited range of resistances. Therefore, in order to obtain consistent performance, the resistance encountered by the power source must remain within this effective heating range of the power source. The electrical resistance of a structure depends generally on both the specific resistivity of the materials that comprise the structure, as well as its geometry. The specific resistance of a fluid flowing within the elongate body 102, as well as that of the materials used in forming the elongate body and the heater 110 are known. This means the remaining unknown variation in resistance is likely to come from variations in the geometry of the components (e.g., movement of the electrodes with respect to each other, etc.). By minimizing this geometric variation, the spacers can enable more consistent performance of the fluid enhanced ablation system.

Furthermore, the spacers can allow for a simplified manufacturing process in assembling fluid enhanced ablation devices. As mentioned above, the spacers can easily be extruded and cut to size or formed by selectively removing coatings from electrically conductive wires, etc. These components can then be easily placed within the inner lumen of an elongate body and positioned using, for example, interference fits and adhesive materials, or they can be allowed to float within the inner lumen.

Yet another benefit of the designs disclosed herein is that they provide for the uniform heating of fluid flowing through the inner lumen of an elongate body. One problem commonly encountered with heating fluid by passing RF energy between electrodes is the localized boiling of fluid that occurs in areas where the current density is particularly high. For example, if two electrodes (e.g., two wires) are located very close to each other, there can be a disproportionately high current flux in the small space between the electrodes when compared to the current flux seen in other areas of the volume surrounding the electrodes. As a result, fluid flowing through the small space between the electrodes can become super-heated and may boil. This is undesirable because it could cause medical complications in a patient (e.g., by introducing gas bubbles into the blood flow of the heart). Accordingly, it is desirable to achieve the most uniform heating of fluid possible so as to minimize boiling during heating of fluid within the inner lumen.

Figure 13A:
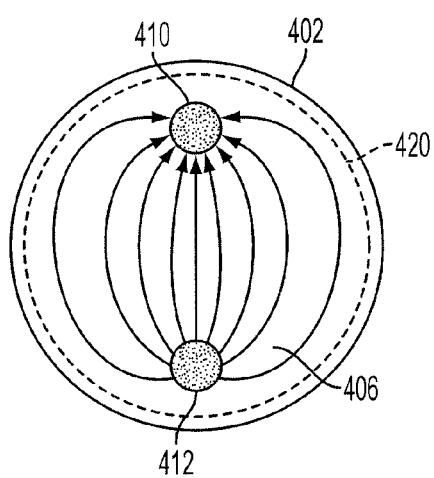
FIG. 13A is a cross-sectional diagram of the elongate body of FIG. 4 at a location adjacent to a spacer element showing simulated lines of current flux.
Figure 13B:
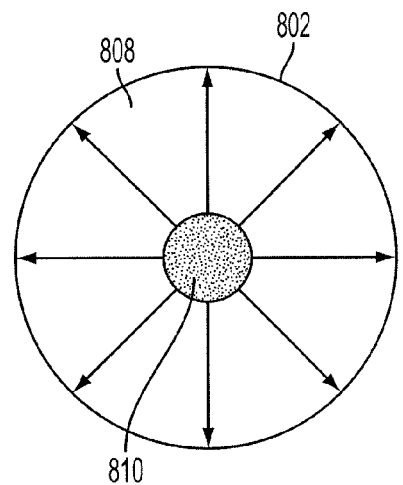
FIG. 13B is a cross-sectional diagram of the elongate body of FIG. 8 at a location adjacent to a spacer element showing simulated lines of current flux.

The spacers disclosed herein aid in the uniform heating of fluid within the inner lumen by maintaining the electrodes used to heat the fluid in a relationship that minimizes areas of disproportionately high current flux between the electrodes. This concept is illustrated in FIGS. 13A and 13B, which depict the dual-wire and single-wire heating assemblies in cross-section with simulated lines of current passing between the two electrodes. FIG. 13A, which illustrates the dual-wire heating assembly shown in FIG. 5C, demonstrates that by maintaining the wires in a separated configuration, the variations in current flux throughout the inner lumen 406 can be minimized. The single-wire heating element depicted in FIGS. 9A and 13B provides an even more uniform current distribution within the inner lumen. As shown in FIG. 13B, current can pass uniformly from around the entire circumference of the wire 810 into the elongate body 802. This results in very uniform heating of the fluid disposed within the inner lumen 806.

Applicability to Other Forms of Ablation

Those that are knowledgeable in the art will recognize that the heating mechanism for producing hyperthermia within the target tissue sufficient to destroy it can include other forms of energy. Ultrasonic vibrational energy is known to be absorbed by tissue and converted to heat, as is microwave and light wave electromagnetic energy. Alternative embodiments of may employ ultrasonic transducers, microwave antennas, or light wave diffusers as emitters disposed in the distal end of an elongate body. Light wave electromagnetic energy can fall in a range spanning visible, near-infrared, infrared, and far-infrared radiation, and can be generated by filaments, arc lamps, lasers of various forms (e.g., diodes, semiconductors, or pumps), or by other means. Similarly, the distal end of an elongate body can be adapted to include a heating mechanism such as a resistive wire for heating the tissue through conduction. Regardless of the type of ablation element utilized, the injection of heated liquid into the tissue proximate any of these ablation elements will improve the ability of each device to heat large volumes of tissue. Accordingly, the heating assemblies disclosed herein can be applicable to devices that utilize any of these alternative ablative energy sources. It is also recognized that the delivery device can be any standard medical delivery device, depending on the tissue to be treated. Alternative embodiments can include metallic or nonmetallic needles, sheaths, or introducers.

Methods of Use

As described above, the various embodiments of the devices and systems disclosed herein can be utilized in a variety of procedures to treat a number of medical conditions. For example, medical devices as disclosed herein can be configured for insertion into a target volume of tissue directly during an open surgical procedure or during percutaneous ablation therapy. Alternatively, the medical devices can be configured to be passed through one or more layers of tissue during a laparoscopic or other minimally invasive procedure. Furthermore, the devices can be configured for introduction into a patient via an access port or other opening formed through one or more layers of tissue, or via a natural orifice (i.e., endoscopically). Depending on the device employed, delivery may be facilitated by directly inserting the elongate body as shown in FIG. 2, or by introducing a catheter containing an elongate body through, for example, a patient's circulatory system. Following delivery to a treatment site, a portion of a surgical device, e.g., a distal portion of the elongate body 102, can be inserted into a target treatment volume such that an ablation element is disposed within the treatment volume. In some embodiments, the ablation element can be positioned near the center of the treatment volume.

Once the device is positioned within the treatment volume, fluid can be delivered through the device into the treatment volume. The heating assemblies disclosed herein can be utilized to deliver fluid at a therapeutic temperature, as described above. In addition, the one or more ablation elements can be activated to simultaneously deliver therapeutic energy, such as RF energy, into the tissue in the treatment volume. In some embodiments, however, the one or more ablation elements need not be activated, and therapy can be administered by delivering heated fluid from the elongate body alone. After a period of time, or depending on one or more feedback indications (e.g., a reading from a temperature sensor disposed within the treatment volume), the ablation element can be deactivated along and the flow of fluid into the volume can be stopped. The device can then be removed and/or repositioned if additional therapy is required.

Sterilization and Reuse

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the surgical devices disclosed herein may be disassembled partially or completely. In particular, the elongate body 202 of the medical device 200 shown in FIG. 2 may be removed from the handle 204, or the entire handle and elongate body assembly may be decoupled from the electrical and fluid connections 206, 208. In other embodiments, solely the distal portion of the elongate body 202 (e.g., only the portion that extends into a patient's body) can decouple from a proximal portion that can remain connected to the handle 204. In yet another embodiment, the handle, elongate body, and connections may be removably coupled to a housing that contains, for example, the fluid reservoir, pump, and power supply and controller shown in FIG. 1.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. An ablation device, comprising:
   an elongate body having
      proximal and distal ends,
      an inner lumen extending through the elongate body, and
      at least one outlet port formed in the elongate body configured to deliver fluid to tissue surrounding the elongate body;
   a heating assembly comprising at least two wires extending through the inner lumen, the at least two wires being configured to heat fluid flowing through the inner lumen; and
   at least one spacer disposed within the inner lumen, the at least two wires extending through the at least one spacer such that the at least one spacer is effective to maintain the at least two wires in a substantially fixed geometric relationship with each other.

2. The ablation device of claim 1, further comprising an ablation element disposed along a length of the elongate body adjacent to the at least one outlet port, the ablation element being configured to heat tissue surrounding the ablation element when the elongate body is inserted into tissue.

3. The ablation device of claim 2, further comprising:
   a first power source configured to heat fluid flowing through the inner lumen by passing current between the at least two wires; and
   a second power source configured to heat tissue surrounding the elongate body by passing current between the ablation element and a collector electrode position outside the elongate body.

4. The ablation device of claim 1, further comprising an insulating material disposed on inner walls of the elongate body.

5. The ablation device of claim 4, wherein the insulating material terminates at a position distal to a distal-most of the at least one spacer and proximal to the at least one outlet port formed in the elongate body.

6. The ablation device of claim 1, wherein the at least one spacer includes at least a first spacer and a second spacer distally spaced apart from the first spacer.

7. The ablation device of claim 6, wherein the first spacer is separated from the second spacer by a distance of about 5 mm.

8. The ablation device of claim 6, wherein the first spacer is separated from the second spacer by a distance of about 2 mm.

9. The ablation device of claim 6, wherein the at least two wires are each coated with an insulating material proximal to the first spacer.

10. The ablation device of claim 9, wherein the at least two wires are exposed between the first spacer and the second spacer.

11. The ablation device of claim 10, wherein the at least two wires have a chlorided outer surface extending between the first spacer and the second spacer.

12. The ablation device of claim 1, wherein the at least one spacer has a maximum outer diameter that is less than a diameter of the inner lumen such that the at least one spacer can move radially within the inner lumen.

13. The ablation device of claim 1, wherein the at least one spacer has a maximum outer diameter equal to a diameter of the inner lumen such that the at least one spacer cannot move radially within the inner lumen.

14. The ablation device of claim 1, further comprising at least one temperature sensor disposed within the inner lumen distal to the at least one spacer and configured to measure a temperature of the fluid flowing through the inner lumen.

15. The ablation device of claim 14, further comprising a second temperature sensor disposed within the inner lumen proximal to the at least one spacer and configured to measure a temperature of the fluid flowing through the inner lumen.

16. The ablation device of claim 14, wherein the at least one temperature sensor is a thermocouple.

17. The ablation device of claim 16, wherein the thermocouple is configured to float in the fluid distal of the at least one spacer.

18. The ablation device of claim 14, wherein the at least one temperature sensor is separated from the at least one spacer by a distance of about 10 mm.

19. The ablation device of claim 1, wherein the at least one spacer is a disc-shaped member having two bores configured to receive the at least two wires and a central lumen.

20. The ablation device of claim 19, wherein the two bores have a circular shape and the central lumen has a non-circular shape.

* * * * *